PIN OAK

Filed April 7, 1965 3 Sheets-Sheet 1

INVENTOR.
DAVID B. COLE
BY
Oberlin, Maky & Donnelly
ATTORNEYS

PIN OAK

Filed April 7, 1965 3 Sheets-Sheet 2

INVENTOR.
DAVID B. COLE
BY
Oberlin, Maky & Donnelly
ATTORNEYS

PIN OAK

Filed April 7, 1965 3 Sheets-Sheet 3

INVENTOR.
DAVID B. COLE

BY

Oberlin, Maky & Donnelly
ATTORNEYS

United States Patent Office

Plant Pat. 2,662
Patented August 23, 1966

2,662
PIN OAK

David B. Cole, Mentor, Ohio, assignor to The Cole Nursery Company, Mentor, Ohio, a corporation of Ohio Filed Apr. 7, 1965, Ser. No. 446,441
1 Claim. (Cl. Plt.—51)

This invention relates to a new and distinct variety of *Quercus palustris* (commonly known as pin oak) which originated as a seedling selected from a large planting of pin oak seedlings made by me.

This new variety of pin oak tree is distinguished from other pin oak trees in that the lower branches diverge from the main trunk at angles of generally from about 90° to about 45° upwardly, in contrast to the downwardly inclined or drooping condition normally observed. The tree is very resistant to damage resulting from the weight of snow or ice thereon and is of vigorous, uniform growth habit with exceptionally well-spaced branches.

Pin oak trees have long been utilized in towns and cities as street trees because of their desirable characteristics, but it is recognized that the tendency of the lower branches to droop or diverge downwardly constitutes a most undesirable characteristic, requiring early and repeated pruning to maintain essential head room, both for pedestrians on sidewalks and vehicles near the curb. Such additional maintenance expense has caused this otherwise very desirable tree to be avoided in many instances when selections for street tree plantings have been made.

Whereas a typical mature pin oak tree will have its upper branches diverging from the main trunk in an upward direction, its intermediate branches diverging substantially horizontally, and its lower branches diverging or drooping downwardly to an excessive degree, substantially all of the branches of my new variety of pin oak tree diverge from the main trunk at a definite upward angle.

I have asexually propagated this new variety of pin oak tree at Painesville, Ohio, both by budding and by grafting, and have found that the above-indicated desirable characteristics are consistently perpetuated in the progeny. Grafted trees of this new variety are also now growing at Circleville, Ohio, and demonstrate the same novel characteristics. In 1958, approximately 500 of the new tree of this invention were budded on seedling understock, and in 1959, over 2,000 additional such trees were propagated by budding. Substantial additional propagations have been made in the subsequent years.

Figure 1:
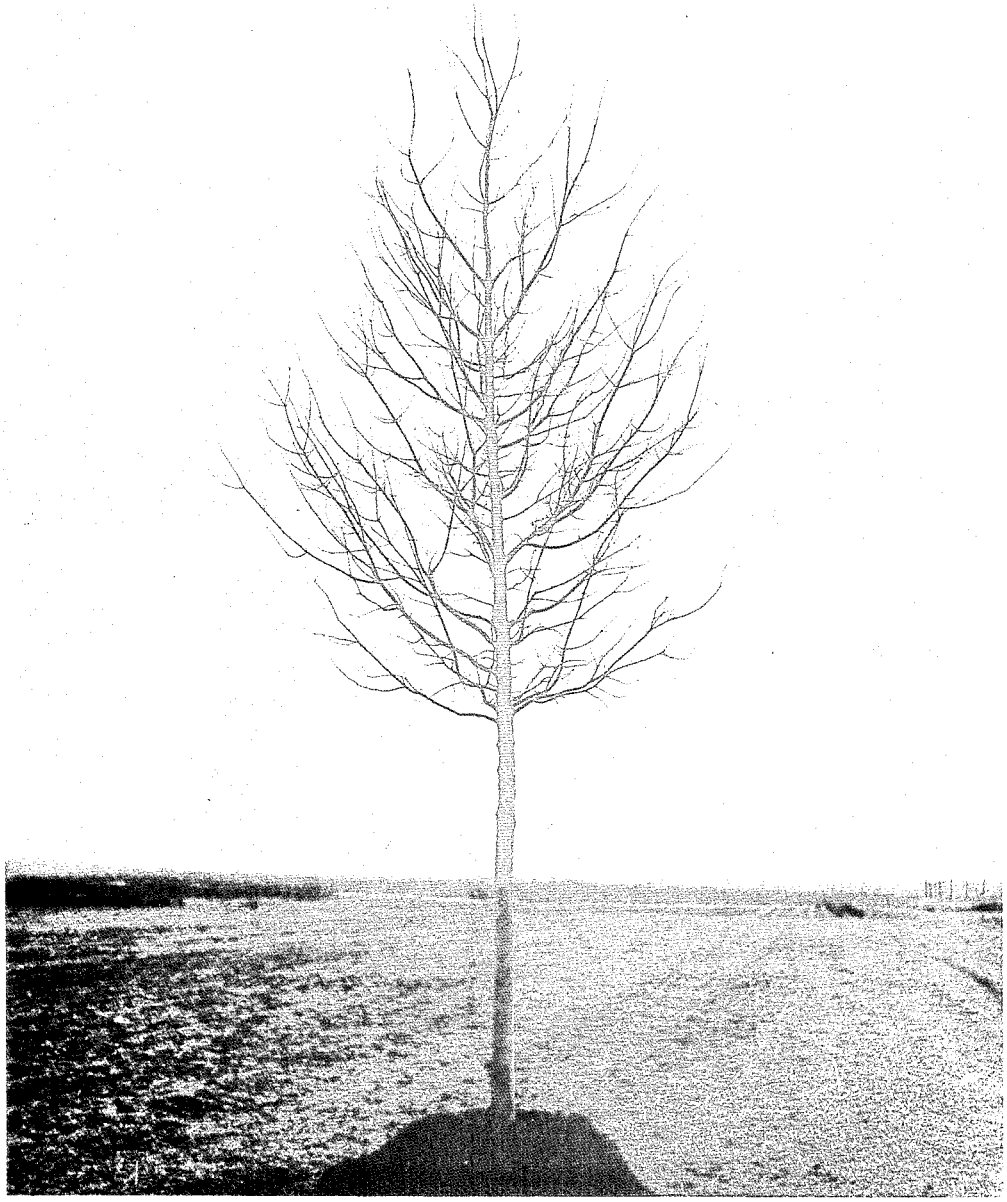
FIG. 1 shows the pin oak tree of this invention in winter after dropping of the foliage.
Figure 2:
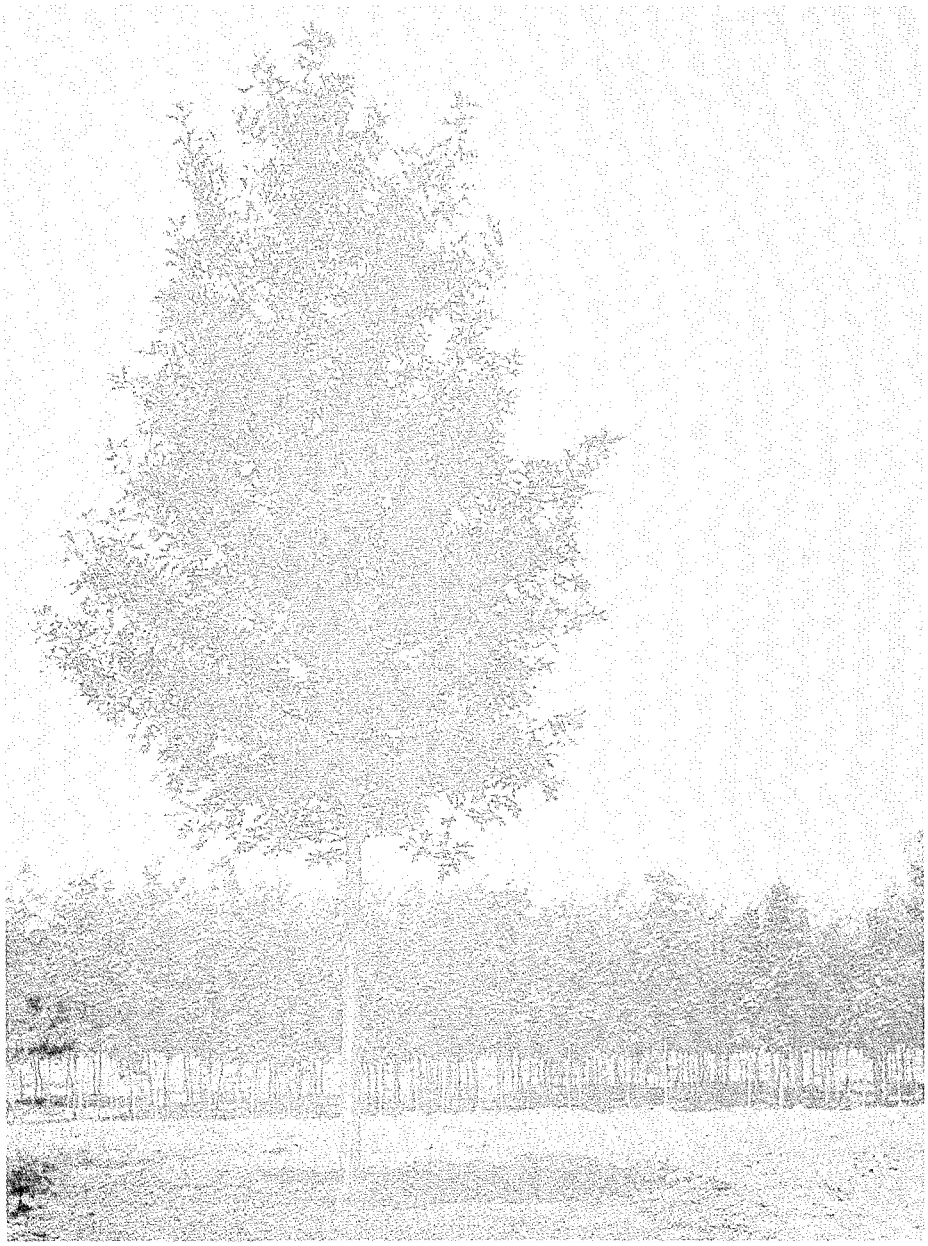
FIG. 2 shows such tree in leaf.
Figure 3:
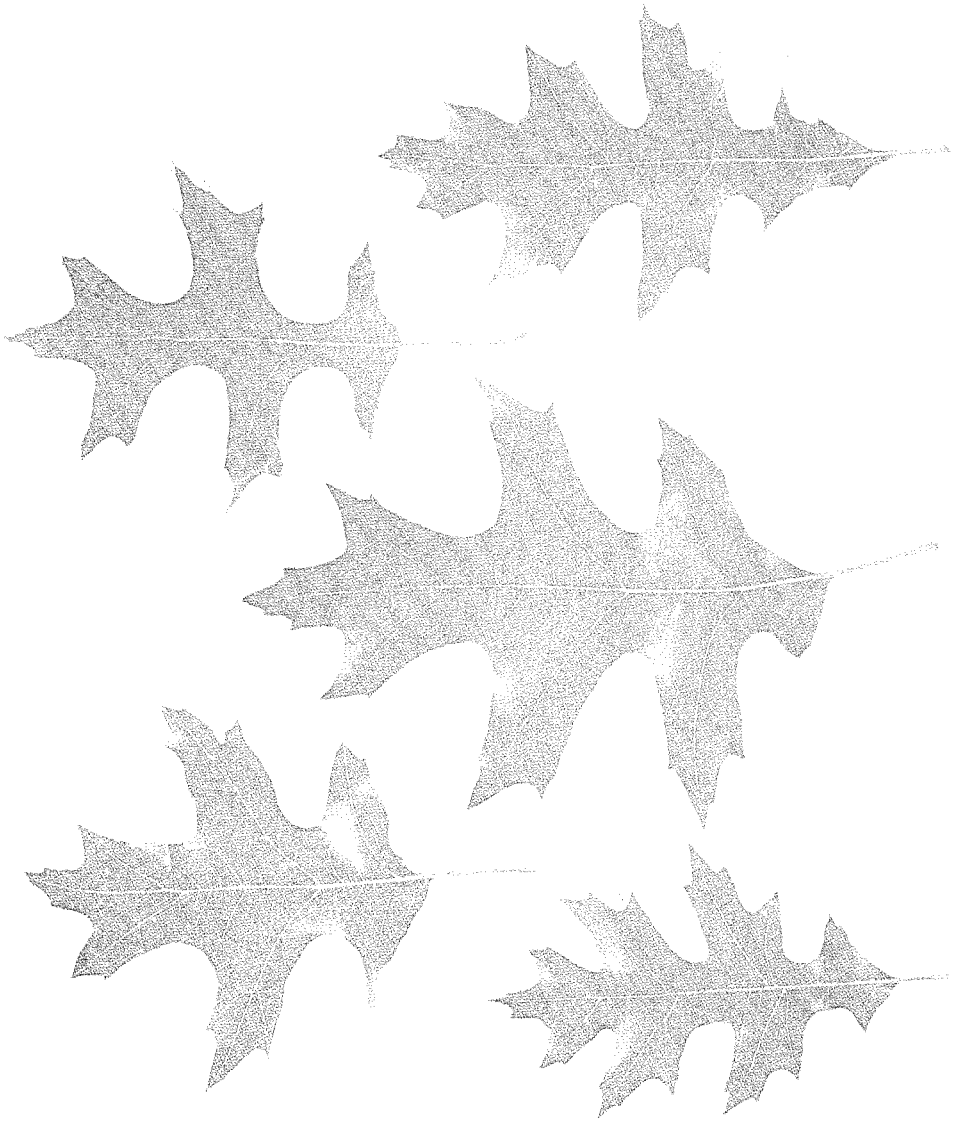
FIG. 3 shows typical leaves from such new tree.

In general, the leaves, buds and bark color do not differ greatly from the species. In 1963, progeny of the original clone six years of age had the following characteristics. The trunk diameter (DBH) was approximately 4 inches with a straight excurrent trunk and short, horizontal or "up-sweep" branches diverging at angles of 45 to 90° from the trunk, and forming a narrow oval or pyramidal head. Height of the tree was approximately 16 feet. The branches are well distributed. The slender branchlets are soon glabrous, greenish or reddish brown. The buds are small, glabrate and reddish brown. The leaves are alternately arranged with lobed margins, 10–15 cm. long and 8–12 cm. wide; mostly with three irregular lobes on each side; the sinuses are deep, often within 1 cm. of the midrib; the leaves are mostly cuneate at the base with tufts of hair in the axils of the veins beneath; the petiole is slender, 2.5 cm. long, bright glossy green above, lighter green beneath; taking on a brilliant red color in the autumn.

I claim:

A new and distinct variety of pin oak tree (*Quercus palustris*) substantially as herein shown and described, characterized particularly as to novelty by its well-spaced lower branches which diverge from the main trunk at angles of generally from 90° to about 45° upwardly, substantially all of the other branches also diverging from the main trunk at upward angles, by the exceptionally vigorous uniform growth habit of the tree, and by resistance to snow and ice damage.

No references cited.

ANTONIO F. GUIDA, *Acting Primary Examiner.*

R. E. BAGWILL, *Assistant Examiner.*